US011103476B2

(12) United States Patent
Takeo et al.

(10) Patent No.: US 11,103,476 B2
(45) Date of Patent: *Aug. 31, 2021

(54) COMPOSITION FOR EXTERNAL USE ON SKIN FOR INFLAMMATORY DISEASES

(71) Applicant: NIPPON SUISAN KAISHA, LTD., Tokyo (JP)

(72) Inventors: Jiro Takeo, Hachioji (JP); Hiroyuki Kawahara, Hachioji (JP)

(73) Assignee: NIPPON SUISAN KAISHA, LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/689,689

(22) Filed: Nov. 20, 2019

(65) Prior Publication Data
US 2020/0108038 A1 Apr. 9, 2020

Related U.S. Application Data

(63) Continuation of application No. 14/928,369, filed on Oct. 30, 2015, now Pat. No. 10,525,028, which is a continuation of application No. 14/117,330, filed as application No. PCT/JP2012/062114 on May 11, 2012, now Pat. No. 9,220,702.

(30) Foreign Application Priority Data

May 12, 2011 (JP) .................. 2011-107512

(51) Int. Cl.
| *A61K 31/202* | (2006.01) |
| *A61K 47/06* | (2006.01) |
| *A61K 31/683* | (2006.01) |
| *A61P 17/00* | (2006.01) |
| *A61P 17/04* | (2006.01) |
| *A61K 31/232* | (2006.01) |
| *A61K 31/685* | (2006.01) |
| *A61K 31/7032* | (2006.01) |
| *A61K 9/00* | (2006.01) |

(52) U.S. Cl.
CPC .......... *A61K 31/202* (2013.01); *A61K 9/0014* (2013.01); *A61K 31/232* (2013.01); *A61K 31/683* (2013.01); *A61K 31/685* (2013.01); *A61K 31/7032* (2013.01); *A61K 47/06* (2013.01); *A61P 17/00* (2018.01); *A61P 17/04* (2018.01)

(58) Field of Classification Search
None
See application file for complete search history.

(56) References Cited

U.S. PATENT DOCUMENTS

| 5,145,686 A | 9/1992 | Horrobin et al. |
| 5,668,174 A | 9/1997 | Kawagishi et al. |
| 5,709,855 A | 1/1998 | Bockow |
| 5,847,000 A | 12/1998 | Horrobin et al. |
| 5,914,347 A | 6/1999 | Grinda |
| 6,177,470 B1 | 1/2001 | Horrobin et al. |
| 8,536,223 B2 | 9/2013 | Kelliher et al. |
| 9,220,702 B2 | 12/2015 | Takeo et al. |
| 10,525,028 B2* | 1/2020 | Takeo .................. A61P 17/06 |
| 2001/0021522 A1 | 9/2001 | Kawashima et al. |
| 2003/0166723 A1 | 9/2003 | Nakajima et al. |
| 2008/0108699 A1 | 5/2008 | Tateishi et al. |
| 2012/0142773 A1 | 6/2012 | Kelliher et al. |
| 2016/0317592 A1 | 11/2016 | Yamaguchi et al. |

FOREIGN PATENT DOCUMENTS

| DE | 202008006708 U1 | 4/2008 |
| EP | 0085579 A2 | 8/1983 |
| EP | 0173478 A1 | 3/1986 |
| EP | 0454102 A2 | 10/1991 |
| EP | 0611569 A1 | 8/1994 |
| EP | 0675120 A2 | 10/1995 |
| GB | 2327347 A | 1/1998 |
| JP | S58208217 A | 12/1983 |
| JP | 7233062 A | 9/1995 |
| JP | H10218731 A | 8/1998 |
| JP | H10508287 A | 8/1998 |
| JP | 200247176 A | 2/2002 |
| JP | 3354581 B2 | 12/2002 |
| JP | 2006219454 A | 8/2006 |
| WO | 2006085687 A1 | 8/2006 |
| WO | 2010125340 A1 | 11/2010 |

OTHER PUBLICATIONS

EPO Office Action corresponding to EP Patent Application No. 12781963.9 dated Apr. 23, 2020.
Verbey et al., "Modulation of immunogenic keratitis in rabbits by topical administration of poly-unsaturated fatty acids," Current Eye Research, vol. 7, No. 6, 1988; pp. 549-556.
A. Anstey et al., "Topical Evening Primrose Oil as Treatement for atopic exzema" Journal of Dermotological Treatment (1990) 1, 199-201, 3 pages.
Extended European Search Report corresponding to Application No. 12781963.9-1460/2708230 PCT/JP2012062114; dated Nov. 4, 2014.
International Search Report for International Application No. PCT/JP2012/062114; dated Jun. 12, 2012, with English Translation.
Jareonkitmongkol et al., "Production of Dihomo-(gamma)-Linolenic Acid by a (delta)5-Desaturase-Defective Mutant of Mortierella alpina 1S-4," Jul. 1992, Applied and Environmental Microbiology, vol. 58, No. 7, pp. 2196-2200.

(Continued)

Primary Examiner — My-Chau T. Tran
(74) Attorney, Agent, or Firm — Cantor Colburn LLP

(57) ABSTRACT

[Problem] To provide a composition for external skin use that has anti-inflammatory and antiallergic activity, and is very safe. [Solution] A composition for external skin use for inflammatory diseases contains dihomo-gamma-linolenic acid (DGLA) as the active ingredient thereof. It is preferable for the DGLA to be present as a glyceride, a phospholipid, or an alkyl ester. The amount of DGLA contained in the composition for external use is 0.1-50 wt %.

7 Claims, 8 Drawing Sheets

(56) References Cited

OTHER PUBLICATIONS

Kawashima et al., "Industrial Production of Dihomo-(gamma)-linolenic Acid by a (delta)5-Desaturase-defective Mutant of Mortierella alpina 1S-4 Fungus," 2000, JAOCS, (Journal of the American Oil Chemists Society), vol. 77, No. 11, pp. 1135-1138, 2000.
N.L. Morse et al., "A Meta-Analysis of Randomized, Placebo-Controlled Clinical Trials of Efamol Evening Primrose Oil in Atopic Eczema. Where Do We Go from Here in Light of More Recent Discoveries?" Current Pharmaceutical Biotechnology, 2006, vol. 7, pp. 503-524.
R. Foster et al., "Borage oil in the treatment of atopic dermatitis," Nutritional Journal 26; pp. 708-718; 2010.
T. Brosche et al., "Effect of borage oil consumption on fatty acid metabolism, transepidemial water loss and skin parameters in elderly people," Archives of Gerontology and Geriatrics; Vo. 30, pp. 139-150; 2000.
United States Non Final Office Action corresponding to U.S. Appl. No. 14/117,330, dated Mar. 6, 2015.
USPTO Final Office Action corresponding to U.S. Appl. No. 14/928,369; dated May 15, 2018.
USPTO Non-Final Office Action & Non-Compliant Amendment corresponding to U.S. Appl. No. 14/928,369; dated Jun. 5, 2017.
USPTO Notice of Allowance corresponding to U.S. Appl. No. 14/928,369; dated Aug. 21, 2019.

\* cited by examiner

*; P<0.05 (Kruskal-Wallis test, Dunn's multiple comparison test)

*; P<0.05(Kruskal-Wallis test, Dunn's multiple comparison test)

*; P<0.05(Kruskal-Wallis test, Dunn's multiple comparison test)

COMPOSITION FOR EXTERNAL USE ON SKIN FOR INFLAMMATORY DISEASES

The present application is a continuation application of U.S. patent application Ser. No. 14/928,369, filed on Oct. 30, 2015 and U.S. patent application Ser. No. 14/117,330, filed on Nov. 12, 2013, the entire contents of which are incorporated herein by reference. The application Ser. No. 14/117,330 is the U.S. National stage of application No. PCT/JP2012/062114, filed May 11, 2012. Priority under 35 U.S.C. § 119(a) and 35 U.S.C. § 365(b) is hereby claimed from Japanese Application No. 2011-107512, filed May 12, 2011, priority to which is also claimed herein, and the contents of which are also incorporated by reference herein.

TECHNICAL FIELD

The present invention relates to a composition for external use on skin that has therapeutic effect on various kinds of inflammatory disease such as dermatitis such as atopic dermatitis, contact dermatitis or UV-caused skin disorder, and rheumatism, psoriasis and lupus.

BACKGROUND ART

As our living environment is changing or becoming complex or with recent changes in our food life, cases of allergic skin disease are rapidly increasing in number. Exemplary allergic skin diseases are atopic dermatitis and contact dermatitis. Various methods are currently employed to treat these allergic skin diseases and they include avoidance of allergens through a better living environment or a dietary therapy and the administration of anti-allergic agents or steroids. As of today, however, no completely effective method has yet been established to treat allergic skin diseases and a therapeutic drug is desired that is safe to use without developing any side effects and which is capable of exhibiting satisfactory therapeutic efficacy.

Dihomo-γ-linolenic acid (8,11,14-eicosatrienoic acid), which is hereinafter abbreviated as DGLA, is an n-6 polyunsaturated fatty acid contained in breast milk, fish oil, seaweeds, meats, etc. and may be synthesized in vivo from linolic acid via γ-linolenic acid. Heretofore, the physiological actions of the orally administered DGLA precursor γ-linolenic acid have been studied to yield numerous reports concerning hypertension, arterial infarction, complications of diabetes mellitus (neuropathy), and rheumatism, and a lot of cases have also been reported concerning diseases such as atopic dermatitis that involve allergic inflammations (for example, Non-Patent Document 1). A possible anti-inflammatory mechanism of orally administered γ-linolenic acid is speculated to start with conversion of γ-linolenic acid to DGLA which in turn is metabolized by cyclooxigenase or 15-lipoxygenase into prostaglandin E1 (PGE1) which competes with prostaglandin E2 or into 15-hydroxyeicosatrienoic acid (15-HETrE) which inhibits 5-lipoxygenase. As for DGLA, partly because of the lack of a process for its mass production, fewer clinical reports have been published than for γ-linolenic acid. Recently, however, a microorganism-based technology for DGLA production was discovered (Patent Document 1) and an atopy-like dermatitis suppressing action (Patent Document 2) and an anti-arterial infarction action have been reported from experiments with animal models. In those experiments, however, the feed was a mixed diet containing a DGLA oil which was administered orally.

Few studies have been reported on the use of γ-linolenic acid or DGLA as agents for external use, and in the single clinical report of the case where a cream using a γ-linolenic acid containing oil was used in patients with atopic dermatitis, some improvement was recognized in a self-appraisal by the patients themselves but no significant difference was recognized in a doctor's appraisal (Non-Patent Document 2.)

Patent Documents 3 and 4 suggest that essential fatty acids including DGLA be used as agents for external use for skin disease but no working examples were given. Patent Document 5 discloses the COX-2 inhibitory action of DGLA and suggests that it is used in inflammatory skin disease.

CITATION LIST

Patent Documents

Patent Document 1: JP 3354581
Patent Document 2: WO 2006/085687
Patent Document 3: EP 0173478
Patent Document 4: EP 0085579
Patent Document 5: WO 2010/125340

Non-Patent Documents

Non-Patent Document 1: Current Pharmaceutical Biotechnology, 7, p 503-524, 2006. "A Meta-Analysis of Randomized, Placebo-Controlled Clinical Trials of Efamol (Trade Mark) Evening Primrose Oil in Atopic Eczema. Where Do We Go from Here in Light of More Recent Discoveries?"
Non-Patent Document 2: J. Dermatological Treatment, 1, p 199-201, 1990, "Topical evening primrose oil as treatment for atopic eczema."

SUMMARY OF INVENTION

Technical Problem

The object of the present invention is to provide a composition for external use on skin that is safe to use and has an anti-inflammatory action. Drugs of first choice currently used to treat chronic skin diseases such as atopic dermatitis are agents for external use such as steroids and the immunosuppressant FK-506 (common name: tacrolimus; trade name: Protopic). Although showing a potent anti-inflammatory action, these drugs are suspected to cause side effects, so they are directly administered to the diseased area as an agent for external use to reduce the possibility of systemic side effects. Nevertheless, these drugs still have side effects and the advent of a safer agent for external use is desired.

The term composition for external use as used herein means compositions that are to be directly applied to the skin, as exemplified by pharmaceutical drugs for external use, quasi-drugs for external use, and cosmetic products.

The "pharmaceutical drugs" are intended for use in diagnosis, treatment or prevention of diseases in humans or animals; the "cosmetic products" are intended for use on the human body by rubbing, spraying or like methods in order to keep it clean, beautify it, make it more attractive, change the facial appearance, or keep the skin or hair in healthy condition, provided that they exert a mild action on the human body; and the "quasi-drugs" which are intermediate between the two categories have more distinct efficacy than cosmetic products and prevent skin troubles without causing side effects. In countries where no such definitions are available, the composition for external use of the present invention shall be understood in the context of equivalents thereto.

Solution to Problem

Although DGLA has been reported to be effective against skin disease if it is ingested by oral administration, there is no report on the effect that is obtained by using DGLA as an agent for external use on skin. Since highly unsaturated fatty acids including γ-linolenic acid and eicosapentaenoic acid serve as the substrates for enzymes including cyclooxygenase and lipoxygenase which are involved in inflammations and allergy, they have been studied for their possible involvement in inflammations and allergic disease but their effects are so mild that only a few have reached the level of development as pharmaceutical drugs.

While making studies of safer and more efficacious compositions for external use, the present inventors found that DGLA showed an unexpectedly potent action against atopic dermatitis and this finding has led to the accomplishment of the present invention.

The gist of the present invention comprises compositions for external use on skin as recited in (1) to (9) below:
(1) A composition for external use on skin in the treatment of inflammatory disease which comprises dihomo-γ-linolenic acid (DGLA) as an active ingredient.
(2) The composition for external use on skin in the treatment of inflammatory disease as recited in (1), wherein the dihomo-γ-linolenic acid (DGLA) is contained in the form of any one of a glyceride, a phospholipid, a glycolipid, an alkyl ester, a salt, or a free fatty acid.
(3) The composition for external use on skin in the treatment of inflammatory disease as recited in (2), wherein the glyceride is a triglyceride, a diglyceride, or a monoglyceride.
(4) The composition for external use on skin in the treatment of inflammatory disease as recited in (2), wherein the alkyl ester is an ester with a lower $C_{1-4}$ alcohol.
(5) The composition for external use on skin in the treatment of inflammatory disease as recited in (2), wherein the phospholipid is diacylglycerophospholipid or lysoacylglycerophospholipid.
(6) The composition for external use on skin in the treatment of inflammatory disease as recited in any one of (1) to (5), which contains 0.01 to 50 wt % of the dihomo-γ-linolenic acid (DGLA).
(7) The composition for external use on skin in the treatment of inflammatory disease as recited in any one of (1) to (6), wherein the inflammatory disease is an inflammatory skin disease.
(8) The composition for external use on skin in the treatment of inflammatory disease as recited in (7), wherein the inflammatory disease is atopic dermatitis, allergic contact dermatitis, irritant contact dermatitis, psoriasis, rheumatism, or lupus.
(9) The composition for external use on skin as recited in any one of (1) to (8), which is a formulation that contains 0.01 to 50 wt % of the dihomo-γ-linolenic acid (DGLA) and is applied continuously for at least 7 consecutive days to an area affected by the inflammatory disease.
(10) The composition for external use on skin as recited in (9), which is a formulation that contains 0.05 to 10 wt % of the dihomo-γ-linolenic acid (DGLA) and is applied continuously for at least 7 consecutive days to an area affected by the inflammatory disease.
(11) The composition for external use on skin as recited in (9), which is a formulation that contains 0.05 to 7 wt % of the dihomo-γ-linolenic acid (DGLA) and is applied continuously for at least 7 consecutive days to an area affected by the inflammatory disease.
(12) The composition for external use on skin as recited in (9), which is a formulation that contains 0.01 to 50 wt % of the dihomo-γ-linolenic acid (DGLA) and is applied continuously for at least 10 consecutive days to an area affected by the inflammatory disease.
(13) The composition for external use on skin as recited in (9), which is a formulation that contains 0.01 to 50 wt % of the dihomo-γ-linolenic acid (DGLA) and is applied continuously for at least 14 consecutive days to an area affected by the inflammatory disease.
(14) The composition for external use on skin as recited in any one of (1) to (13), which is for suppressing the itch of the inflammatory disease.

Advantageous Effects of Invention

When applied to the skin, the agent for external use of the present invention has therapeutic effect on an inflammatory skin disease or allergic skin disease, as exemplified by atopic dermatitis.

DESCRIPTION OF EMBODIMENTS

Figure 1:
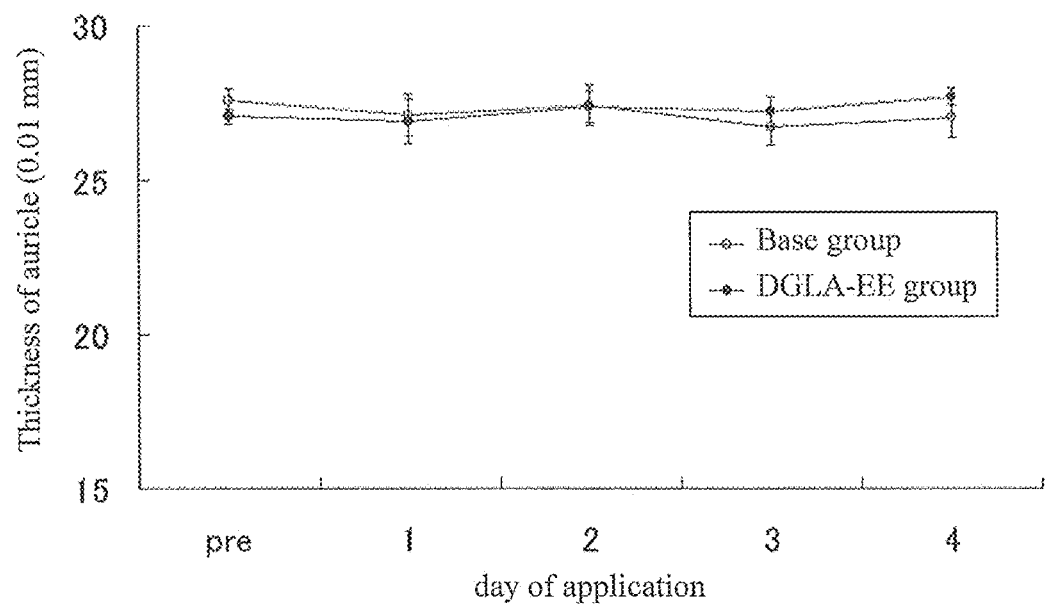
FIG. 1 is a graph showing the results of the skin irritation test conducted in Example 3.
Figure 1:
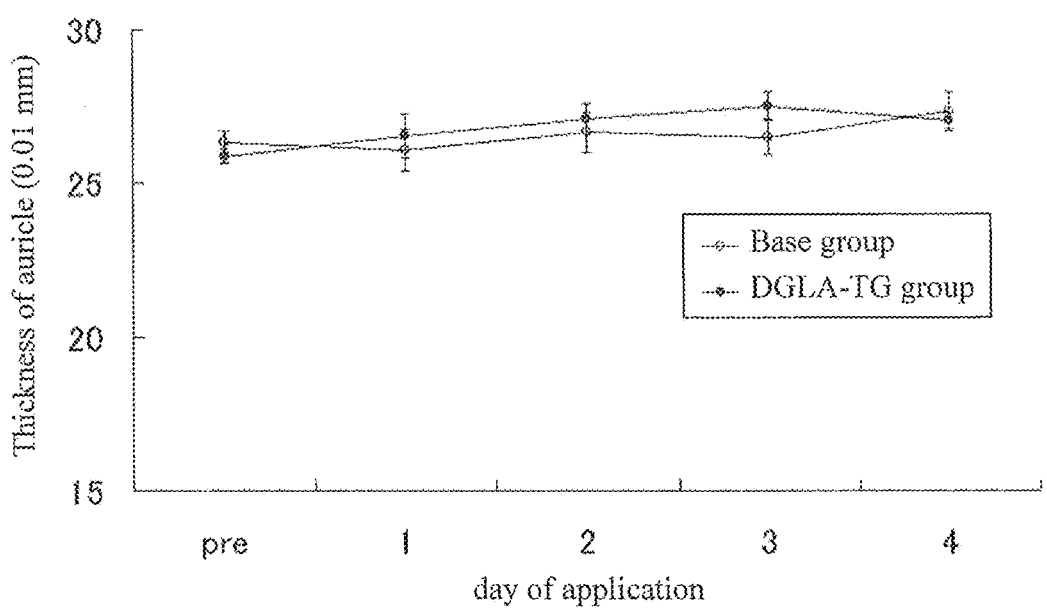

The dihomo-γ-linolenic acid (DGLA) as used in the present invention is an n-6 unsaturated fatty acid with a 20-carbon chain and three double bonds. The DGLA to be used for the purpose of the present invention may take on any form that contains it as a constituent fatty acid and examples include a free fatty acid, salts such as sodium and potassium, lower $C_{1-4}$ alkyl esters such as ethyl ester and methyl ester, glycerin esters such as triglyceride, diglyceride, and monoglyceride, phospholipids such as diacylglycerophospholipid and lysoacylglycerophospholipid, and glycolipids. Preferred are esters such as glycerin esters and lower alkyl esters, with ethyl ester being particularly preferred.

DGLA can be mass-produced by the method publicly disclosed in Japanese Patent No. 3354581. Specifically, a microorganism of the genus *Mortierella* capable of producing a DGLA-containing oil is cultured and the oil is extracted from the cultured cells. The oil as obtained by this method contains 30-50% of DGLA, so it may be immediately used; alternatively, it may be used after enriching the DGLA. Specifically, the DGLA containing oil is subjected to wintering, treatment with an enzyme such as lipase, or the like to enrich the DGLA. In another process, the DGLA containing oil is subjected to hydrolysis or alcoholysis to effect conversion to the free fatty acid, a salt thereof, an ester thereof with a lower alcohol, or the like. If desired, further enrichment may be performed by distillation, urea adduct process, column treatment, enzymatic treatment, supercritical carbon dioxide treatment, or the like.

The pharmaceutical drug for external use, quasi-drug for external use, and the cosmetic product that are provided by the present invention may take on any dosage form that enables the active ingredient to be directly administered to the topical surface of the skin. Examples include ointments such as oleaginous ointments, emulsion ointments (creams) and water-soluble ointments; as well as gels, lotions, tapes, patches, sprays, gels, and reservoir-type patches.

Depending on the need, the composition for external use of the present invention permits the use of any materials that are commonly used in compositions for external use and they include bases, absorption promoters, moisturizers, thickeners, emulsifying agents, colorants, fragrances, antioxidants, stabilizers, sterilizers, and antiseptics.

Bases for external use include, for example, white petrolatum, cetanol, stearyl alcohol, stearic acid, white beeswax, liquid paraffin, lauromacrogol, squalane, squalene, lanolin, isobutyl myristate, and middle-chain fatty acid triglyceride. Since the highly unsaturated fatty acids or their salts or esters are oleaginous, they can be conveniently mixed with oleaginous bases to form a homogeneous mixture. Water-containing bases can also be used if they are emulsions (W/O or O/W type) and the active ingredient can be readily mixed by incorporating it into the oil phase.

Examples of the absorption promoter include urea, crotamiton, diethyl sebacate, diisopropyl adiptate, ethanol, isopropyl alcohol, dimethyl sulfoxide, 1-dodecylazacycloheptan-2-one, 1-menthol, salicylic acid, pyrrolidones, middle-chain fatty acid esters, phosphatidylcholine, silicone-based promoters, and limonene.

Exemplary moisturizers include polyhydric alcohols such as glycerin, sorbitol, propylene glycol, 1,3-butanediol, sodium pyrrolidone carboxylic acid, and sodium hyaluronate.

Exemplary thickeners include gum arabic, guar gum, locust bean gum, carrageenan, carboxymethylcellulose, carboxymethylcellulose sodium, polyacrylic acid salts, polyacrylic acid esters, natural latex, vinyl acetate resin emulsion, polyvinyl alcohol, hydroxypropyl cellulose, and hydroxypropyl methylcellulose.

Exemplary emulsifying agents include glycerin fatty acid esters, sucrose fatty acid esters (sugar esters), sorbitan fatty acid esters, propylene glycol fatty acid esters, lecithin, polyoxyethylene fatty acid esters, polyoxyethylene castor oil, polyoxyethylene hardened castor oil, polyoxyethylene alkyl ethers, polyoxyethylene sorbitan fatty acid esters, and sodium lauryl sulfate.

Exemplary fragrances include *eucalyptus* oil, lavender oil, menthol, peppermint oil, rose oil, orange oil, cherry flavor, fruit flavor, vanillin, and vanilla flavor.

Exemplary antioxidants include L-ascorbic acid, ascorbyl stearate, ascorbyl palmitate, sodium ascorbate, erythorbic acid, sodium erythorbate, isopropyl citrate, dl-α-tocopherol, dl-δ-tocopherol, dibutylhydroxytoluene (BHT), and butylhydroxyanisole (BHA). Among these, ascorbyl palmitate, ascorbyl stearate, L-ascorbic acid, dl-α-tocopherol, dl-δ-tocopherol, or combinations thereof are preferred.

Exemplary stabilizers include polysorbates, polyethylene glycol, ethanol, acetone, light silicic anhydride, and EDTA.

Exemplary antiseptics include parahydroxybenzoic acid esters, benzalkonium chloride, sorbic acid, phenol, chlorobutanol, chlorocresol, and benzyl alcohol.

The composition for external use of the present invention may additionally contain other active principles, such as steroids, anti-allergic agents, immunosuppressants, and anti-inflammatory drugs, which are commonly used for the treatment of inflammatory diseases including various types of dermatitis, rheumatism, psoriasis, and lupus.

The composition for external use of the present invention is useful against inflammatory diseases including various types of dermatitis, rheumatism, and psoriasis that have been shown to be effectively treated with highly unsaturated fatty acids. Stated specifically, the composition can be directly applied to areas affected by atopic dermatitis, allergic contact dermatitis, irritant contact dermatitis, rheumatism, psoriasis, and lupus.

The amount in which the composition for external use of the present invention is to be used is variable over a wide range depending upon such factors as the symptom, the surface area of the region affected by the disease, the age and body weight of the patient, and the mode of drug administration; the general standard dosage is within the range from 0.1 to 5 g per day and this is directly applied to the diseased area once or several times a day.

The concentration of DGLA to be contained in the composition for external use preferably ranges from about 0.01 to about 50 wt %, more preferably from 0.05 to 10 wt % or from 0.05 to 7 wt %. Depending on the relative content of DGLA in DGLA containing oil, a suitable amount of the DGLA containing oil may be mixed in the composition for external use. Since the DGLA itself is in oil form, the required amount of it can be readily mixed in any base for agents for external use.

As will be shown by the results of Example 4 (FIG. 2), the agent for external use on skin of the present invention exhibits a comparable level of efficacy to the Protopic ointment which is currently used as a therapeutic agent for atopic dermatitis. A recommended method of using the agent involves continuous application for at least 7 days, preferably at least 10 days, more preferably at least 14 days. When this agent was administered for 3 weeks, the clinical symptom score of atopic dermatitis could be lowered to a level comparable to that achieved by the Protopic ointment. The continuous application may be substantially continuous or continuous with an interval of one or two days as exemplified by a two-week application, with 5 days per week.

The followings show exemplary formulations for the composition for external use of the present invention. The concentrations of the DGLA containing oil that are indicated in the tables may be increased or decreased as appropriate.

(1) Oleaginous Base

[White Ointment]

TABLE 1

| Ingredient | Content (in 100 g) |
| --- | --- |
| DGLA containing oil | 5.0 g |
| White beeswax | 4.75 g |
| Sorbitan sesquioleate | 1.9 g |
| White petrolatum | bal. |

[White Petrolatum]

TABLE 2

| Ingredient | Content (in 100 g) |
| --- | --- |
| DGLA containing oil | 5.0 g |
| White petrolatum | 95.0 g |

(2) Emulsion Base

[Hydrophilic Ointment]

TABLE 3

| Ingredient | Content (in 100 g) |
| --- | --- |
| DGLA containing oil | 5.0 g |
| White petrolatum | 23.75 g |
| Stearyl alcohol | 19.0 g |
| Propylene glycol | 11.4 g |
| Polyoxyethylene hardened castor oil 60 | 3.8 g |
| Glyceryl monostearate | 0.95 g |
| Methyl parahydroxybenzoate | 0.095 g |
| Propyl parahydroxybenzoate | 0.095 g |
| Purified water | bal. |

[Purified Lanolin]

TABLE 4

| Ingredient | Content (in 100 g) |
| --- | --- |
| DGLA containing oil | 5.0 g |
| Purified lanolin | 95.0 g |

[Absorptive Ointment]

TABLE 5

| Ingredient | Content (in 100 g) |
| --- | --- |
| DGLA containing oil | 5.0 g |
| White petrolatum | 38.0 g |
| Cetyl alcohol | 9.5 g |
| White beeswax | 4.75 g |
| Sorbitan sesquioleate | 4.75 g |
| Lauromacrogol | 0.475 g |
| Methyl parahydroxybenzoate | 0.095 g |
| Propyl paraohydroxybenzoate | 0.095 g |
| Purified water | bal. |

(3) Zinc Oxide Ointment

TABLE 6

| Ingredient | Content (in 100 g) |
| --- | --- |
| DGLA containing oil | 5.0 g |
| Zinc oxide | 19.0 g |
| Liquid paraffin | 2.85 g |
| White ointment | bal. |

(4) Urea Cream

TABLE 7

| Ingredient | Content (in 100 g) |
| --- | --- |
| DGLA containing oil | 5.0 g |
| Urea | 4.75 g |
| Cetyl alcohol | 4.75 g |
| Glyceryl monostearate | 4.75 g |
| Liquid paraffin | 4.75 g |
| Glycerin | 9.5 g |
| Polyoxyethylene(20) cetyl ether | 2.375 g |
| Methylpolysiloxane | 0.95 g |
| Methyl parahydroxybenzoate | 0.19 g |
| Tetrasodium edetate | 0.19 g |
| Sodium citrate | 0.19 g |
| Purified water | bal. |

On the following pages, working examples of the present invention are set out but they are by no means intended to limit the scope of the present invention.

Unless otherwise noted, all indications of percentages in the working examples are on a weight basis.

EXAMPLE 1

Preparation of DGLA Ethyl Ester (DGLA-EE) and DGLA Containing Triglyceride (DGLA-TG)

A DGLA containing oil was obtained by the method described in U.S. Pat. No. 3,354,581. Specifically, 500 mL of hexane was added to 200 g of dried cells of a filamentous fungus (Mortierella alpine) and the mixture was stirred and filtered; by repeating these steps three times, an oil fraction was extracted and the hexane layer was evaporated to give a DGLA containing oil.

The resulting DGLA containing oil was analyzed for the fatty acid composition. A portion (25 μL) of the oil was collected in a test tube and after adding 1.5 mL of a 0.5N aqueous solution of sodium hydroxide, the mixture was stirred well while it was heated at 80° C. for 5 minutes in a nitrogen gas stream. Thereafter, 2 mL of a reagent solution consisting of 14% boron trifluoride in methanol was added and the mixture was stirred well while it was heated at 80° C. for 80 minutes in a nitrogen gas stream. After the heating, the mixture was air-cooled to approximately between 30° C. and 40° C. and following the addition of isooctane (2 mL), the mixture was vigorously agitated for one minute in a nitrogen gas stream; thereafter, 5 mL of saturated saline was added and the mixture was allowed to stand at room temperature. The separating isooctane layer was recovered and used as a sample in gas chromatography to analyze the fatty acid composition. Indicated below are the conditions for measurement by gas chromatography. The results are shown in Table 8; the values in Table 8 refer to the proportions (%) of the respective fatty acids, with the total quantity of the fatty acids being taken as 100%. The DGLA containing oil was found to contain about 39.8 area % of DGLA.

<Conditions for Measurement by Gas Chromatography>
Apparatus: 6890N Network GC System (Agilent)
Column: DB-WAX (Agilent J&W); 30 m (length)×0.250 mm (inside diameter)×0.25 μm (membrane thickness)
Column temperature: initial temperature, 180° C.; temperature elevation, 3° C./min; final temperature, 230° C.; retained for 15 minutes
Injection port temperature: 250° C.
Detector temperature: 250° C.
Detector: FID
Carrier gas: helium

TABLE 8

Fatty Acid Composition in DGLA Containing Oil

| Fatty acid | Composition (%) |
| --- | --- |
| C16:0 | 16.1 |
| C18:0 | 7.3 |
| C18:1 n-9 | 8.5 |
| C18:2 n-6 | 6.7 |
| C18:3 n-6 | 2.9 |
| C18:3 n-3 | 0.6 |
| C20:0 | 0.8 |
| C20:3 n-6 | 39.8 |
| C20:4 n-6 | 0.7 |
| C22:0 | 2.6 |
| C24:0 | 9.2 |

[Preparation of DGLA-EE]

An egg-plant shaped flask was charged with 15 g of the DGLA containing oil, 5 mL of ethanol and 1.73 mL of 20% sodium ethoxide/ethanol, and the mixture was refluxed in an oil bath (115° C.) for 120 minutes. The reaction mixture was distributed between hexane and water and the hexane layer was evaporated to give 15.4 g of a crude product. The crude product was fractionated with a silica gel column (eluent: hexane/ethyl acetate=15:1) and after collecting the ethyl ester fractions, the solvent was distilled off to give 11.4 g of DGLA-EE. After adding 0.5% (w/w) of δ-tocopherol, the product was used as DGLA-EE in the following working examples.

[Preparation of DGLA-TG]

Fifteen grams of the DGLA containing oil was fractionated with a silica gel column (eluent:hexane:ethyl acetate=10:1) and after collecting the triglyceride fractions, the solvent was distilled off to give 12.5 g of DGLA-TG. After adding 0.5% (w/w) of δ-tocopherol, the product was used as DGLA-TG in the following working examples.

EXAMPLE 2

Preparation of DGLA Ointments

The above-mentioned DGLA-EE or DGLA-TG (10 wt %), white petrolatum (89.95 wt %), and ascorbyl palmitate (0.05 wt %) were mixed under heating at 60° C. to prepare two kinds of DGLA containing ointment. The concentration of DGLA in each ointment was about 4%. A mixture of white petrolatum (99.95 wt %) and ascorbyl palmitate (0.05 wt %) was used as a negative control.

EXAMPLE 3

Skin Irritation Test

To the left auricle of each 6-week old, male ddy mice, a suitable amount of the base (negative control) was applied whereas a suitable amount of the DGLA-EE containing ointment or the DGLA-TG containing ointment was applied to the right auricle of the same individual; both applications were conducted once daily for 5 consecutive days; thereafter, the thickness of each auricle was measured and its state was observed (n=6). In addition, 100 mg of each ointment was applied to the back of 6-week old, male ddy mice once daily for 5 consecutive days and the state of the dorsal skin was observed (n=2). As a result, as shown in FIG. 1, no significant change was recognized in either group as regards the thickness of auricle. The states of each auricle and the dorsal skin were observed and inflammation or the like was not recognized. These findings led to the conclusion that both the DGLA-TG containing ointment and the DGLA-EE containing ointment would be highly safe compositions for external use.

EXAMPLE 4

Effect on Atopic Dermatitis Model Mice

Using NC/Nga mice, which served as a model for spontaneous atopic dermatitis, the anti-inflammatory action of the DGLA containing ointments was examined.

[Test Method]

Four groups (7 animals per a group) of NC/Nga mice that had spontaneously developed symptoms of atopic dermatitis were provided and to the respective groups, the DGLA-TG containing ointment, the DGLA-EE containing ointment, the Protopic ointment as the positive control (product of Astellas Pharma Inc.; containing 0.1% tacrolimus), and the base as the negative control were applied and the resulting changes in dermal symptoms were evaluated in scores. In addition, the effects on scratching behavior as an index of itch were quantitatively analyzed with SCLABA-Real® (Noveltec Inc., Kobe).

[Grouping]

The animals that developed erythema, edema and scabbing on the neck and dorsal part during the period of acclimatization were carefully shaven over the area extending from the back of the head through the back of the neck to the dorsal part and those animals that had moderate symptoms of dermatitis such as erythema, edema and scabbing in the neck or the dorsal part were selected at intervals of several days and grouped in such a way that the clinical symptom scores would be as uniform as possible among the groups.

[Administration of Test Substances]

To the shaven neck and dorsal part, about 100 mg of each test substance was applied once daily for three weeks on a 5-days-a-week basis. Each application was conducted every day from 10:00 to 12:00.

[Items of Observation]

The symptomatic state of the outer surface of the site to which each test substance had been applied was observed before the test, twice a week during the administration, and the day after the final application, and the clinical symptom scores of the symptoms on the neck and dorsal part were recorded based upon the following descriptions of classification.

(1) Symptom scoring criteria (neck and dorsal part score criteria)
1) Items of Observation
  pruritus/itching
  erythema/hemorrhage
  edema
  excoriation/erosion
  scaling/dryness
2) Grading
  The above-mentioned items of observation were graded by the scores given below.

| 0 | No Symptoms |
| 1 | Light |
| 2 | Moderate |
| 3 | Severe |

(2) Body Weight Measurement

Body weight measurement was conducted the day before the start of application, as well as at days 8, 15 and 22 thereafter (day 22 corresponding to the day after final application).

(3) Scratch Counting

The day before the start of application and at day 22 thereafter (the day after final application), scratch counting was performed. Scratching frequency was measured for 20 minutes using an automatic scratching analyzing system (SCLABA-Real® of Noveltec).

[Results]

Figure 2:
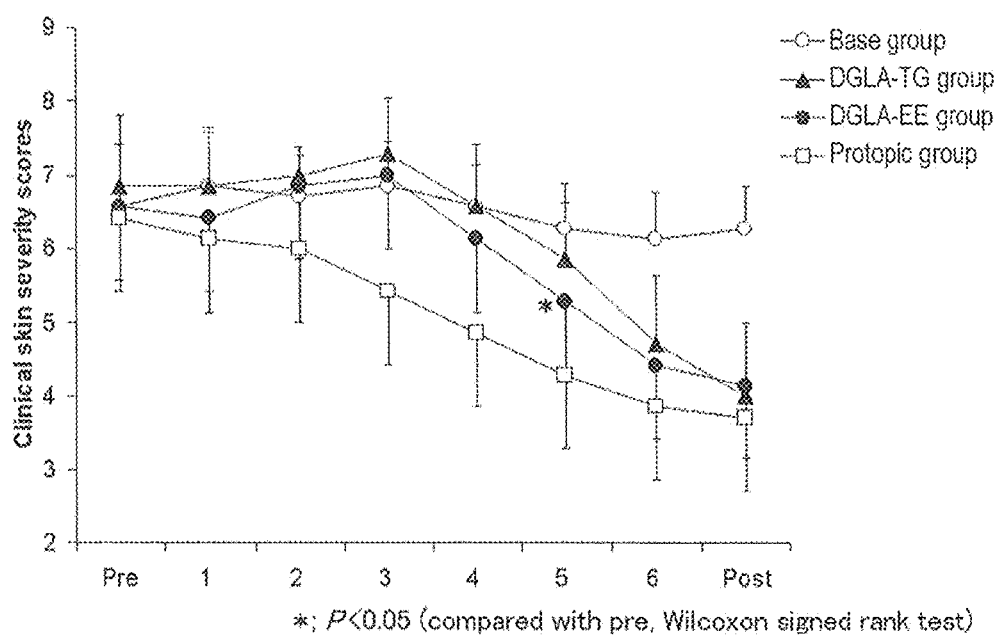
FIG. 2 is a graph showing the changes in clinical symptom scores as observed in Example 4, the data being indicated by the mean±S.E. for mice in groups each consisting of 7 animals. *: $p<0.05$, Wilcoxon signed rank test.

(1) Changes in Clinical Symptom Scores (FIG. 2)

Figure 3:
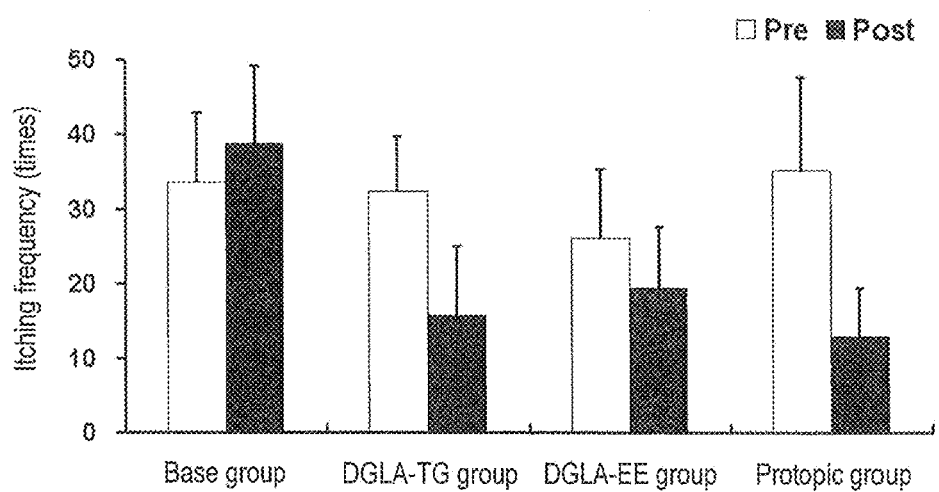
FIG. 3 graphically shows the changes in scratching behavior (scratching frequency and duration in 20 minutes) as observed in Example 4, the data being indicated by the mean±S.E. for mice in groups each consisting of 7 animals.
Figure 3:
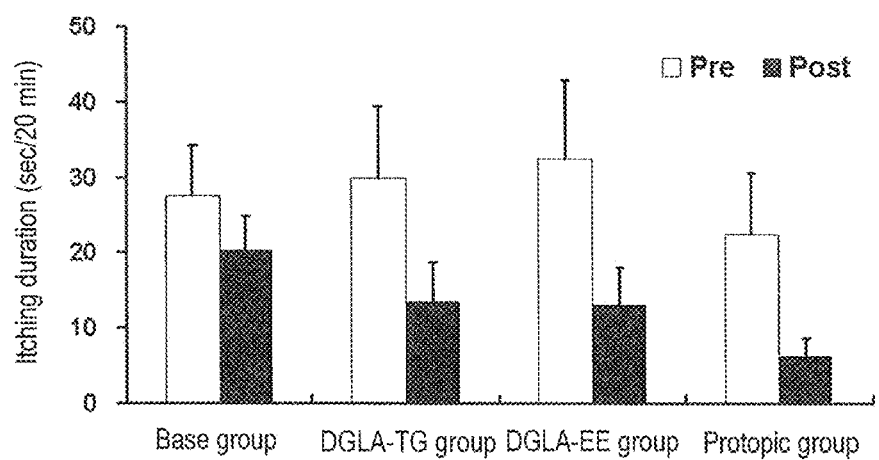

The clinical symptom scores prior to the test were 6.4-6.9 on average in each group (moderate manifestation), with no statistical difference recognized between groups. In the DGLA-TG and DGLA-EE groups, the clinical symptom scores started to improve from the second to third weeks and, in particular, the dermatitis score for the fifth evaluation (at week 3) to the DGLA-EE group showed a statistically significant drop compared to the score before the start of the test (pre) ($p<0.05$, Wilcoxon signed rank test). In the Protopic group, the improvement tended to occur earlier, from the first to second weeks. In any event, at the time the test ended, there was no difference in dermatitis scores among the three groups, the DGLA-TG group, the DGLA-EE group, and the Protopic group, and they were recognized to be comparable in dermatitis suppressing action (2) Changes in Scratching Behavior (FIG. 3)

The frequency and duration of scratching behavior were measured for 20 minutes before the start of the test and no statistical difference was recognized between groups. When measured after the end of the test, the frequency and duration of scratching behavior tended to decrease in each of the DGLA-TG group, the DGLA-EE group, and the Protopic group, but no statistical difference was recognized.

Figure 4:
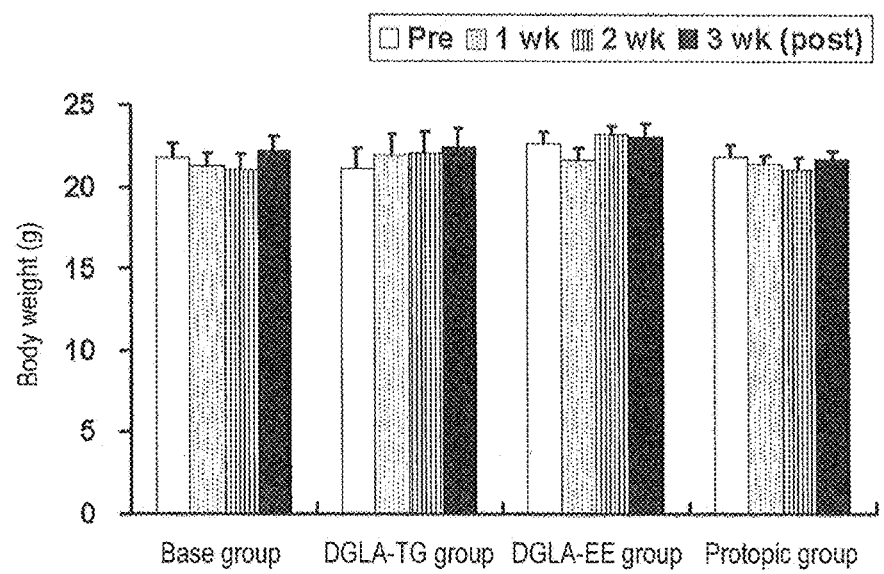
FIG. 4 is a graph showing the changes in body weight as observed in Example 4, the data being indicated by the mean±S.E. for mice in groups each consisting of 7 animals.

(3) Changes in Body Weight (FIG. 4)

Throughout the test period, no statistically marked difference was recognized between groups as regards the average body weight.

As shown above, both the DGLA-TG containing ointment and the DGLA-EE containing ointment had an immunosuppressive effect, which was by no means inferior to the Protopic ointment which is currently used as the drug of first choice against atopic dermatitis and the like.

EXAMPLE 5

A test was conducted with atopic dermatitis model mice to compare the effect of the ethyl ester type DGLA-EE with that of the free type DGLA. The test method was essentially the same as described in Example 4; about 100 mg of each test substance was applied to the shaven neck and dorsal part once daily for 4 weeks on a five-days-a-week basis.

Preparation of DGLA Containing Ointments

A DGLA-EE or DGLA containing ointment was prepared by mixing DGLA-EE or DGLA with white petrolatum as in Example 2 so that the concentration of DGLA-EE or DGLA would be about 10%. Note that DGLA was obtained by hydrolyzing DGLA-EE with potassium hydroxide.

[Results]

Figure 5:
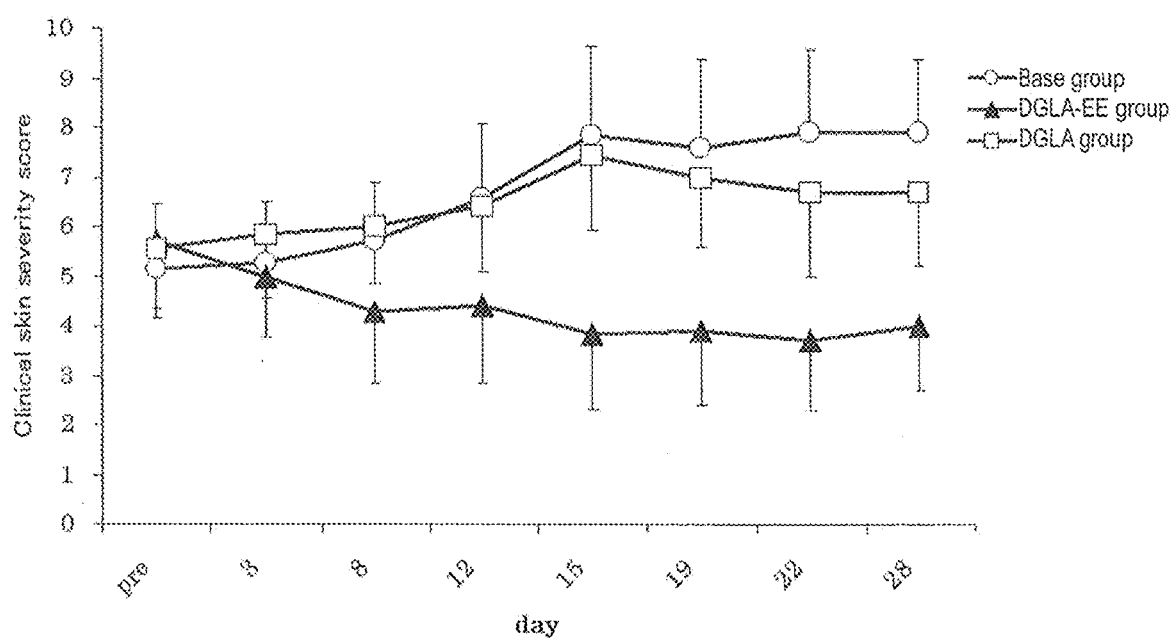
FIG. 5 is a graph showing the changes in clinical symptom scores as observed in Example 5, the data being indicated by the mean±S.E. for mice in groups each consisting of 7 animals.

(1) Changes in Clinical Symptom Scores (FIG. 5)

The clinical symptom scores prior to the test were 5.1-5.7 on average in each group (moderate manifestation), with no statistical difference recognized between groups. Four weeks later, the symptoms of the base group worsened as indicated by a score of 7.9, whereas the symptom score of the DGLA-EE ointment group tended to improve, as indicated by the value of 4.0. The DGLA ointment group showed a slight tendency to improve as compared with the base group, whereas the efficacy was not as great as in the DGLA-EE ointment group. It is therefore concluded that DGLA as an agent for external use preferably takes on the form of an ethyl ester.

Figure 6:
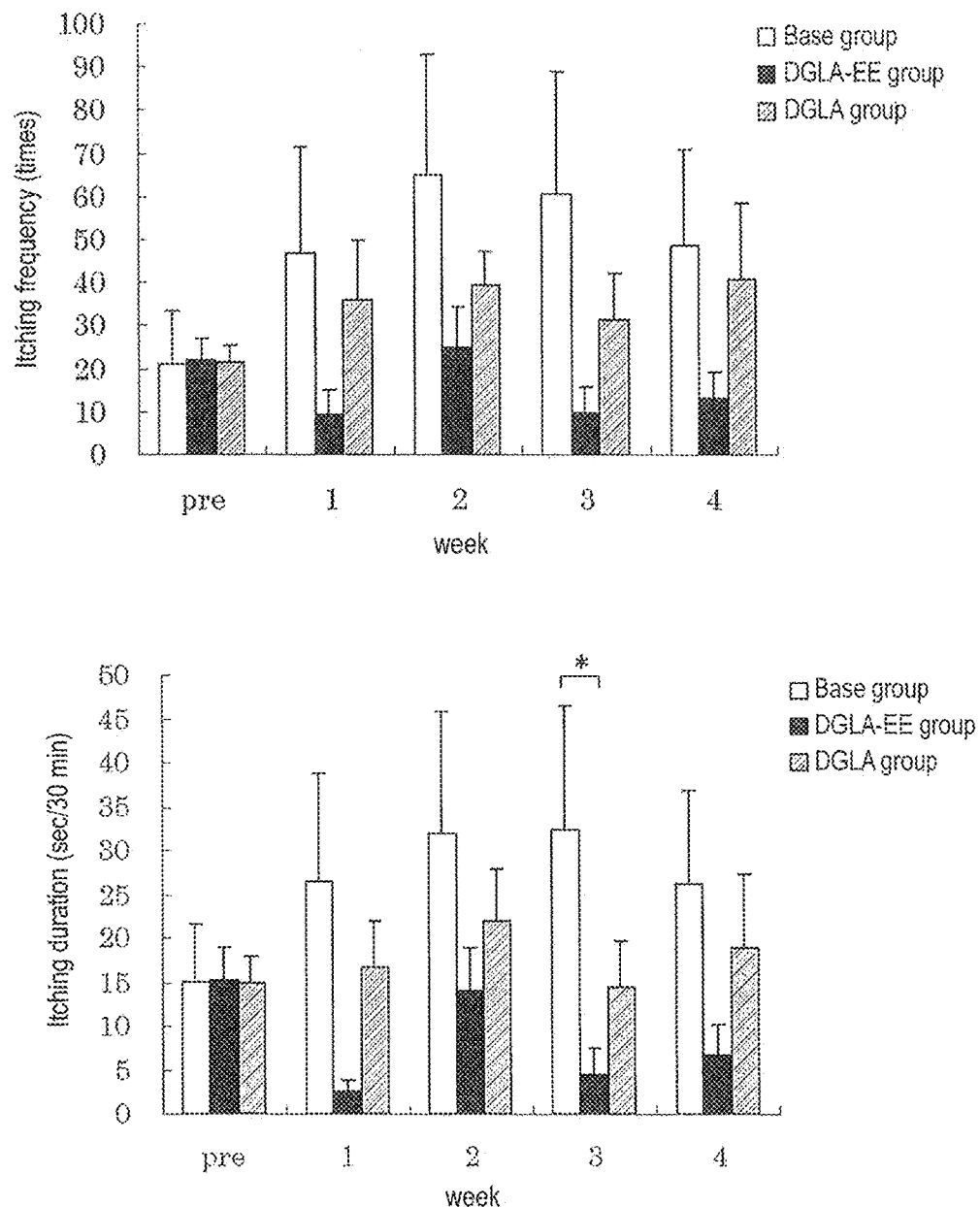
FIG. 6 graphically shows the changes in scratching behavior (scratching frequency and duration in 30 minutes) as observed in Example 5, the data being indicated by the mean±S.E. for mice in groups each consisting of 7 animals. *: $p<0.05$, Kruscal-Wallis test, Dunn's multiple comparison test.

(2) Changes in Scratching Behavior (FIG. 6)

The frequency of scratching behavior was measured within a period of 30 minutes before the start of the test and no statistical difference was recognized between groups. When measured after 4 weeks following the start of the test, both the DGLA-EE ointment group and the DGLA ointment group tended to improve the frequency of scratching behavior as compared with the base group and, particularly in the DGLA-EE ointment group, the frequency of scratching behavior decreased to 13.3 on average as compared with 48.6 for the base group. As for the duration of scratching behavior that was measured within a period of 30 minutes, no statistical difference was recognized between groups before the start of the test; when the test ended 4 weeks later, however, both the DGLA-EE ointment group and the DGLA ointment group had been improved in the duration of scratching behavior and, particularly in the DGLA-EE ointment group, the duration of scratching behavior at week 3 was 4.5 seconds, which was a significant decrease from the value of 32.5 seconds for the base group ($p<0.05$, Kruscal-Wallis test, Dunn's multiple comparison test).

EXAMPLE 6

A test was conducted with atopic dermatitis model mice to study the dose dependency of the DGLA-EE containing ointment. The test method was essentially the same as described in Example 4, except that the transepidermal water loss (TEWL) was an additional item of measurement; about 100 mg of the test substance was applied to the shaven neck and dorsal part once daily for 4 weeks on a five-days-a-week basis.

Preparation of DGLA Ointments

DGLA-EE containing ointments were prepared by mixing DGLA-EE with white petrolatum so that the concentration of DGLA-EE would be 5, 10, and 20%.

[Item of Observation]

The transepidermal water loss (TEWL) was measured before the start of the test as well as at weeks 2 and 4. The measurement was conducted with a multi probe adapter (CK Electronic GmbH, Germany); the sensing probe was pressed against the site on the neck and dorsal part skin where the test substance had been applied and a substantially uniform pressure was maintained until the reading stabilized; three measurements were conducted and their average was taken.

[Results]

Figure 7:
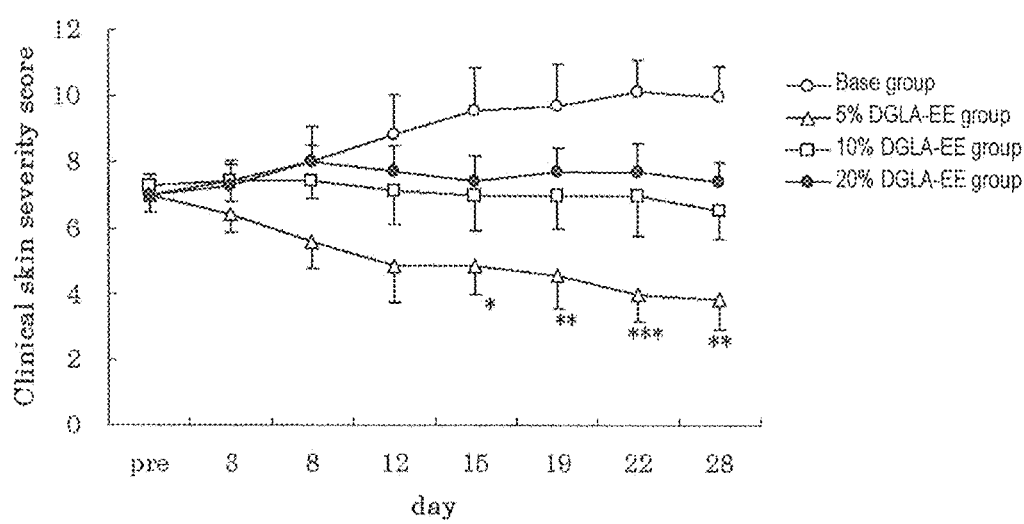
FIG. 7 is a graph showing the changes in clinical symptom scores as observed in Example 6, the data being indicated by the mean±S.E. for mice in groups each consisting of 7 animals. *: $p<0.05$, : $p<0.01$, *: $p<0.001$, Kruscal-Wallis test, Dunn's multiple comparison test.

(1) Changes in Clinical Symptom Scores (FIG. 7)

The clinical symptom scores prior to the test were 7.0-7.3 on average in each group (moderate manifestation), with no statistical difference recognized between groups. Four weeks later, the symptoms of the base group worsened as indicated by a score of 10.0, whereas the symptom scores of the DGLA-EE groups improved in a dose-dependent manner. In particular, the score of the 5% DGLA-E ointment group significantly decreased to 3.9 as compared with the base group (p<0.01, Kruscal-Wallis test, Dunn's multiple comparison test).

Figure 8:
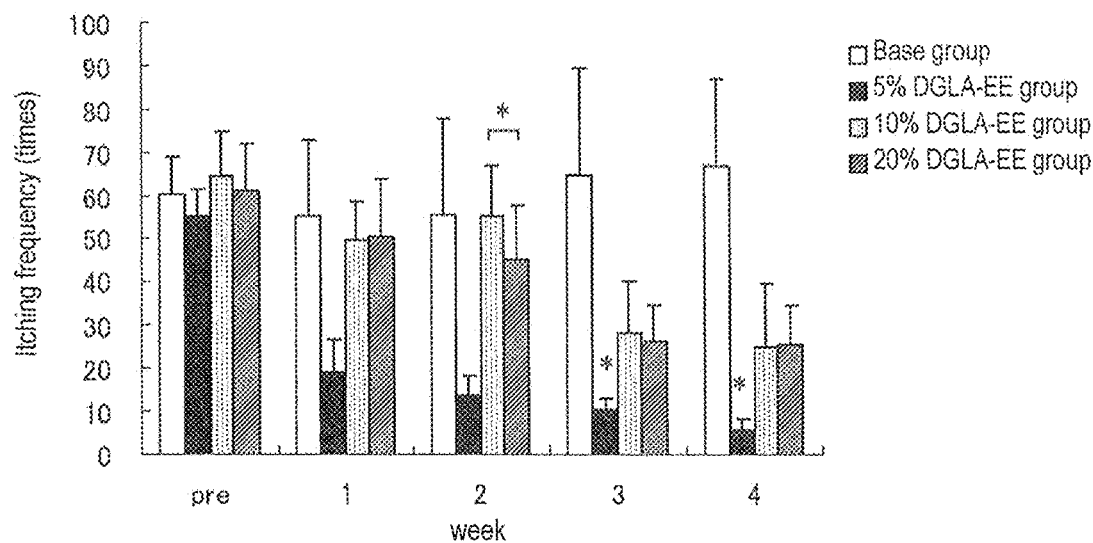
FIG. 8 graphically shows the changes in scratching behavior (scratching frequency and duration in 30 minutes) as observed in Example 6, the data being indicated by the mean±S.E. for mice in groups each consisting of 7 animals. *: $p<0.05$, Kruscal-Wallis test, Dunn's multiple comparison test.
Figure 8:
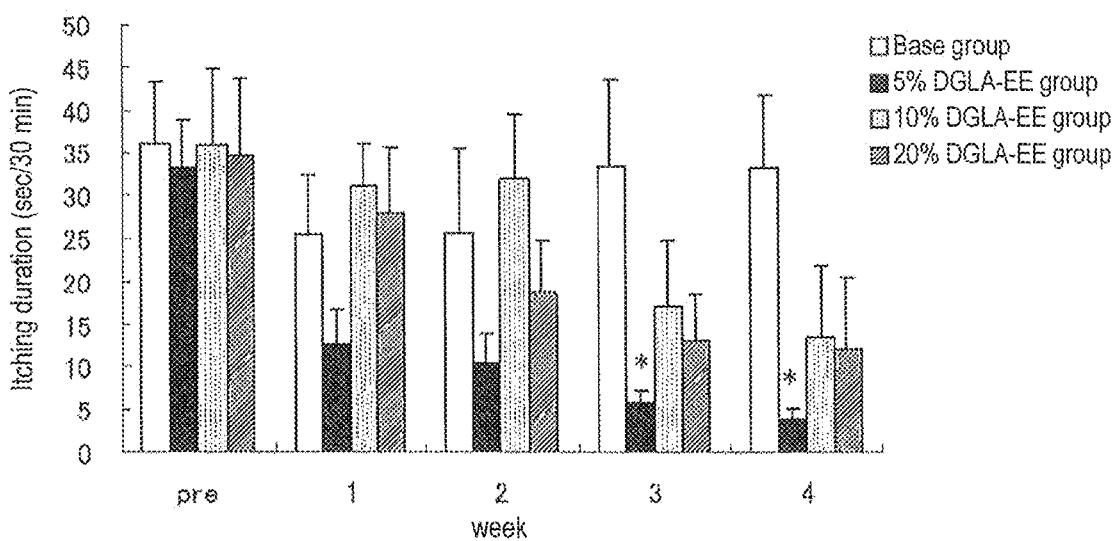

(2) Changes in Scratching Behavior (FIG. 8)

The frequency of scratching behavior was measured within a period of 30 minutes before the start of the test and no statistical difference was recognized between groups. When measured after 4 weeks following the start of the test, each of the DGLA-EE ointment groups tended to improve the frequency of scratching behavior as compared with the base group in a dose-dependent manner and, particularly in the 5% DGLA-EE ointment group, the frequency of scratching behavior significantly decreased to 6.0 as compared with the value of 67.0 for the base group (p<0.05, Kruscal-Wallis test, Dunn's multiple comparison test). As for the duration of scratching behavior that was measured within a period of 30 minutes, no statistical difference was recognized between groups before the start of the test; when the test ended 4 weeks later, however, each of the DGLA-EE ointment groups had improved the duration of scratching behavior in a dose-dependent manner and, particularly in the 5% DGLA-EE ointment group, the duration of scratching behavior was 3.9 seconds, which was a significant decrease from 33.1 seconds for the base group (p<0.05, Kruscal-Wallis test, Dunn's multiple comparison test).

Figure 9:
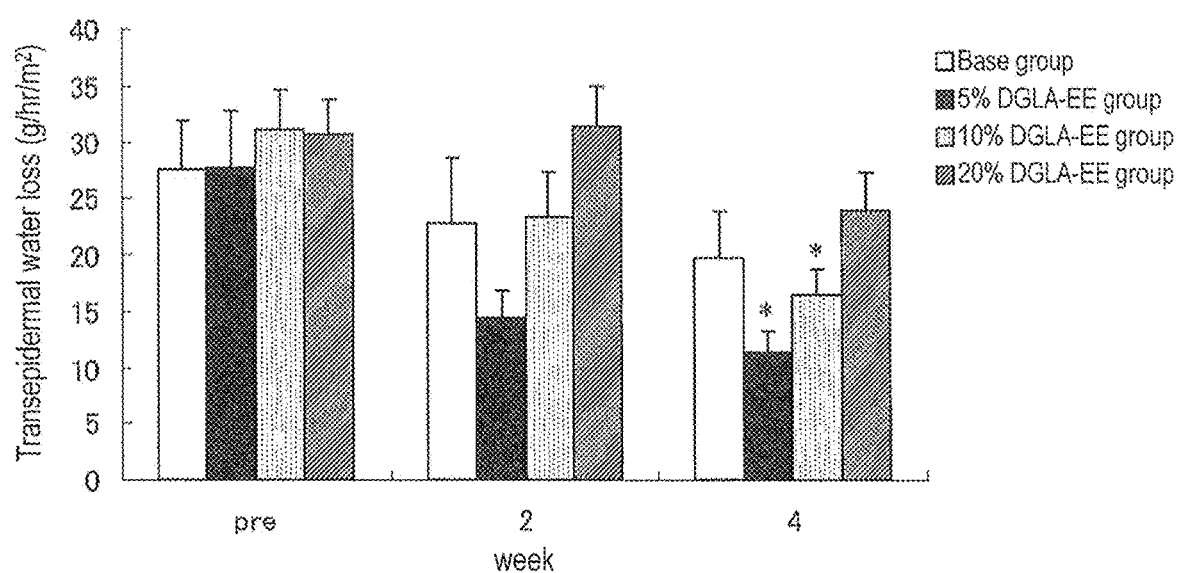
FIG. 9 is a graph showing the changes in transepidermal water loss as observed in Example 6, the data being indicated by the mean±S.E. for mice in groups each consisting of 7 animals. *: $p<0.05$, Kruscal-Wallis test, Dunn's multiple comparison test.

(3) Transepidermal Water Loss (FIG. 9)

In the 5% DGLA-EE ointment group and the 10% DGLA-EE ointment group, TEWL was 27.8 and 31.1 g/hr/m$^2$, respectively, before the start of the test; after 4 weeks following the start of the test, however, they significantly dropped to 11.5 and 16.5 g/hr/m$^2$ (p<0.05, Kruscal-Wallis test, Dunn's multiple comparison test). On the other hand, no significant difference occurred between groups at each week of measurement.

These findings demonstrated that DGLA has an action of improving symptoms of atopic dermatitis and, in particular, it has an itch suppressing action.

INDUSTRIAL APPLICABILITY

The present invention provides an agent for external use on skin that is safe to use and effective against inflammatory diseases.

The invention claimed is:

1. A method of keeping skin in healthy condition, comprising
administering topically, to the skin of a human, an effective amount of dihomo-γ-linolenic acid (DGLA) as an active ingredient in a cosmetic product,
wherein the DGLA is provided in the form of an oil derived from a culture of micro-organisms of genus *Mortierella*, and
wherein the DGLA is applied continuously for at least 14 consecutive days to the skin.

2. The method according to claim 1, wherein the dihomo-γ-linolenic acid (DGLA) is in the form of any one of a glyceride, a phospholipid, a glycolipid, an alkyl ester, a salt, or a free fatty acid.

3. The method according to claim 2, wherein the glyceride is a triglyceride, a diglyceride, or a monoglyceride.

4. The method according to claim 2, wherein the alkyl ester is an ester with a lower $C_{1-4}$ alcohol.

5. The method according to claim 2, wherein the phospholipid is diacylglycerophospholipid or lysoacylglycerophospholipid.

6. The method according to claim 1, wherein the dihomo-γ-linolenic acid (DGLA) is administered in a composition containing 0.01 to 50 wt % of the dihomo-γ-linolenic acid (DGLA).

7. The method according to claim 1, wherein the DGLA is administered in the form of an ointment comprising DGLA containing oil and zinc oxide.

* * * * *